United States Patent

Meier et al.

[11] Patent Number: 5,834,639
[45] Date of Patent: Nov. 10, 1998

[54] METHOD AND APPARATUS FOR DETERMINING CAUSES OF FAULTS IN YARNS, ROVINGS AND SLIVERS

[75] Inventors: Rudolf Meier, Glattfelden; Peter F. Aemmer, Wettswil, both of Switzerland

[73] Assignee: Zellweger Luwa AG, Switzerland

[21] Appl. No.: 460,822

[22] Filed: Jun. 2, 1995

[30] Foreign Application Priority Data

Jun. 2, 1994 [CH] Switzerland .................. 01 727/94

[51] Int. Cl.[6] .................................................. G06F 15/40
[52] U.S. Cl. ............................................ 73/159; 73/160
[58] Field of Search ............... 73/159, 160; 364/470–64

[56] References Cited

U.S. PATENT DOCUMENTS

| | | | |
|---|---|---|---|
| 4,051,722 | 10/1977 | Feller | 364/470.14 |
| 4,246,748 | 1/1981 | Artzto et al. | 364/470.14 |
| 5,119,308 | 6/1992 | Samoto | 364/470 |
| 5,497,335 | 3/1996 | Hoeller | 364/470.14 |
| 5,592,849 | 1/1997 | Nakade et al. | 364/470.14 |

FOREIGN PATENT DOCUMENTS

WO93/05477  3/1993  WIPO.

*Primary Examiner*—Ronald L. Biegel
*Attorney, Agent, or Firm*—Burns, Doane, Swecker & Mathis, L.L.P.

[57] ABSTRACT

The invention relates to a method and an apparatus for recording causes of faults in products, in which the faults are recorded and counted. The recorded faults are represented according to selected parameters, so that a fault pattern is obtained. From this, a reference to the cause of the fault is produced.

9 Claims, 9 Drawing Sheets

METHOD AND APPARATUS FOR DETERMINING CAUSES OF FAULTS IN YARNS, ROVINGS AND SLIVERS

FIELD OF THE INVENTION

The invention relates to a method and an apparatus for determining production-related causes of faults in yarns, rovings and slivers.

BACKGROUND OF THE INVENTION

Faults in textile products, such as yarns, rovings and slivers, can basically have two causes. Either the cause is in the nature of the raw material or it is in the method by which the product is produced, that is to say in the production process. Both causes can lead to faults which have a similar appearance. Such faults are thick or thin places in a yarn, which extend to a greater or lesser extent, or periodically occurring faults, so-called moiré effects. The invention described hereafter relates solely to particularities or faults, the cause of which is to be sought in the production equipment or production processes.

Very good instruments, by means of which faults in a yarn can be detected, are known. It is customary to rectify disturbing faults in the product by cutting them out. It is customary, furthermore, to draw conclusions from the faults present in yarns as to the use or further treatment of the yarn or as to the quality of the initial material, the raw material.

International Patent Application WO 93/05477 discloses, for example, a system for making a fault diagnosis on production machines and a use of the system on textile machines, in which system the fault diagnosis takes place by means of a knowledge-based evaluation of signals which indicate the quality of the products produced. For this purpose, a so-called knowledge base is used, in which the machine parts of a production machine are described for the purpose of subsequently drawing logical inferences from them. At the same time, these machine parts are imaged in a specially designed hierarchy of rules. Such machine parts are, for example, gearwheels (which are described by the number of their teeth), levers (which are described by their length), etc. Characteristic deviations are determined from signals which are known per se and which are represented in spectrograms that indicate the quality of the textile products produced, and possible fault causes are derived from these deviations.

A limitation of such methods and apparatuses is the fact that only possible causes of periodic faults can be indicated by means of them. One example of these are the so-called moiré effects in slivers or yarns.

The invention, as characterized in the claims has the object of rectifying these defects and of providing a method and an apparatus which make it possible to determine from faults in the products the causes of them in a particularly simple way, insofar as these causes are in the production process.

SUMMARY OF THE INVENTION

The object is achieved, according to the invention, in that, in a first step, the faults in the product are recorded, that is to say are recognized. They are recognized in that measured values of the product exceed one or more threshold values. In a preferred version, a pair of parameters, for example, in the case of a yarn, the cross-section and length of a fault, is critical for recognition. The values of these two parameters can be plotted in a system of rectangular coordinates with the fault length and fault cross-section as the abscissa or the ordinate respectively. This "classification field", thus formed can be divided into a grid consisting of length and cross-section classes. The determined values of the faults recognized are assigned continuously to the predetermined classes, so that a fault pattern or a characteristic is obtained from them. This fault pattern is compared with predetermined model reference patterns which allow conclusions to be drawn as to causes of the recorded faults. The predetermined reference patterns can be determined by prior investigations or can come from experience.

The recording of the faults takes place in a way known per se for yarn, for example, in a yarn-cleaning system which works preferably "on-line" and which monitors a plurality of spinning stations, for example in a rotor spinning machine. An example of a classification system for faults is known from Swiss Patent Specification No. 477,573. Reference quantities or threshold values, which indicate limit values for the identification and classification of faults, are determined empirically on the basis of particular user requirements. During the continuous testing of the yarn, the faults are assigned to the individual classes in a way known per se and are counted for the individual classes. The fault pattern obtained thereby can be represented graphically and also interpreted graphically, in order to draw conclusions as to a fault cause. The fault pattern can likewise also be stored in a digital memory, from which a computer can acquire the values and put them correspondingly in relation to one another, as also takes place precisely by human interpretation from graphically represented patterns.

According to a particular version which is particularly suited for use in rotor spinning machines where all the spinning stations are monitored in a known way by yarn cleaners, all the yarn faults from all the spinning stations are classified in the abovementioned way. An average fault pattern indicating average numbers of faults for each class can be derived from this classification. In parallel with this, a fault pattern is prepared for each spinning station. The fault patterns of each individual spinning station are then compared with the average fault pattern. When the spinning station generates a deviating fault pattern, this is investigated with a view to identifying a possible fault cause by comparing it with previously known fault patterns for known fault causes.

The method according to the invention and the apparatus according to the invention have significant advantages. Fault causes can thereby be determined both in a laboratory by the investigation of random samples or directly in the production process by the investigation of the entire production quantity. The fault source can be traced without any disruptive interference in the production of the product, which means that, as a result even small, otherwise disregarded fault causes can be recognized or that the gradual occurrence of such fault causes can be recorded and tracked from an early stage. Relatively few reference values are sufficient as reference quantities. The comparison between the determined values from production and the reference quantities can thus be carried out by a person or by a computer, for which purpose even simple computers are sufficient. It is also possible to divide a production appliance, that is to say a spinning machine, into relatively few parts and thus store reference values for damage to these few parts and thereby obtain a simple, but useful diagnosis. Moreover, the invention makes it possible to record even non-periodic faults in a product and find their causes.

BRIEF DESCRIPTION OF THE DRAWINGS

The invention is explained in more detail below by means of an example and with reference to the accompanying drawings, in which.

DETAILED DESCRIPTION

Figure 1:
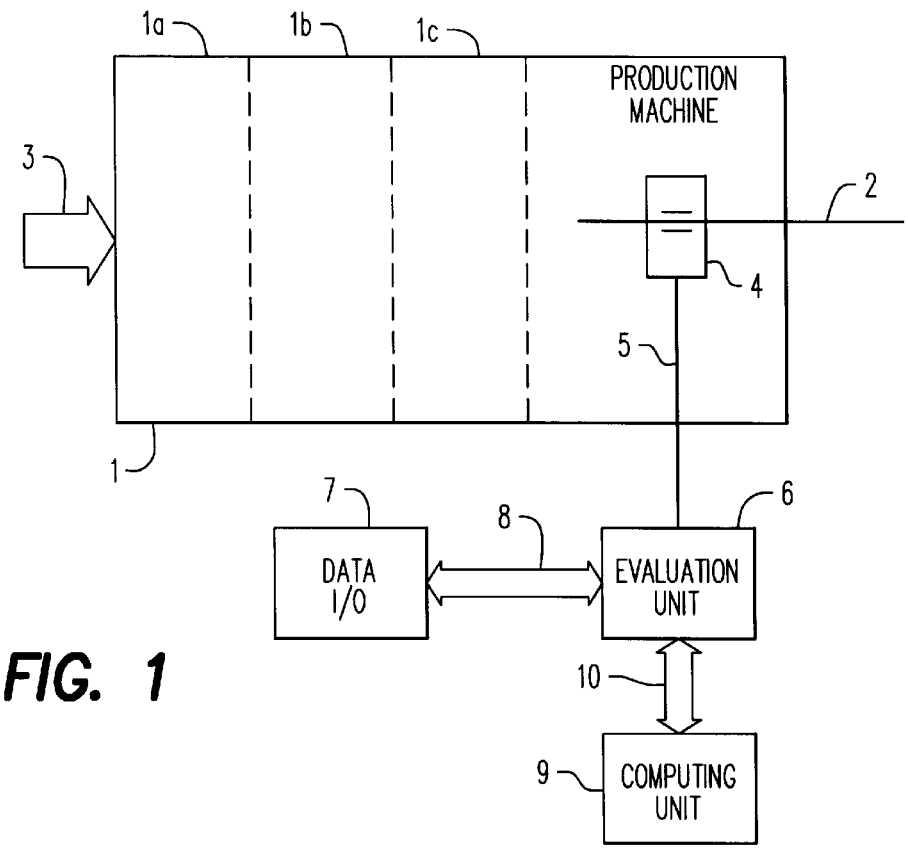
FIG. 1 shows a diagrammatic representation of an apparatus according to the invention in which the product is recorded "on-line"

FIG. 1 shows a production apparatus 1 for a product, such as a yarn, roving or a sliver. The production apparatus 1 can therefore be designed, for example, as a spinning machine, flier, card, drawframe, combing machine, etc., in which, starting from known preliminary products 3, such as, for example, cotton fibres, etc., yarn is produced or a yarn is produced from a sliver. The production apparatus 1 has a sensor 4 known per se, which serves here, for example, as a means for recording faults in a yarn. Specific properties of the yarn 2 can consequently be recorded. The sensor 4 transmits electrical signals by way of a line 5 to an evaluation unit 6 known per se. The sensor 4 and evaluation unit 6 are, for example, part of a known yarn cleaner and thus form both part of a means for recording the faults and part of a means for classifying the faults. The USTER CLASSIMAT is one known example of a means for classifying the faults in a yarn. Specific faults are thereby recorded. Which faults exactly are recorded is determined by permanently set limit values for parameters by which the faults are characterized. The recorded faults, for example the thickenings in the yarn, are classified in relation to the length, that is to say to the quantity of the spun yarn, and are also selectively counted, in that the evaluation unit counts identically classified faults and stores the count values for each class. A computing unit 9 is connected to the evaluation unit 6 by way of a bus 10. The computing unit 9 also comprises a memory, in which are stored reference quantities or combinations of reference quantities which, for example taken together, give a characteristic or a reference pattern. The evaluation unit 6 and computing unit 9 together form a means for counting and classifying the faults and a means for deriving and preparing a fault pattern or reference pattern. For this purpose, the computing unit 9 is provided with a program which operates according to the particulars given below. The data input and output unit 7 can also comprise means for image representation, such as a display screen. It is also to be understood that the computing unit 9 contains a memory, in which predetermined reference patterns can be stored.

Figure 2:
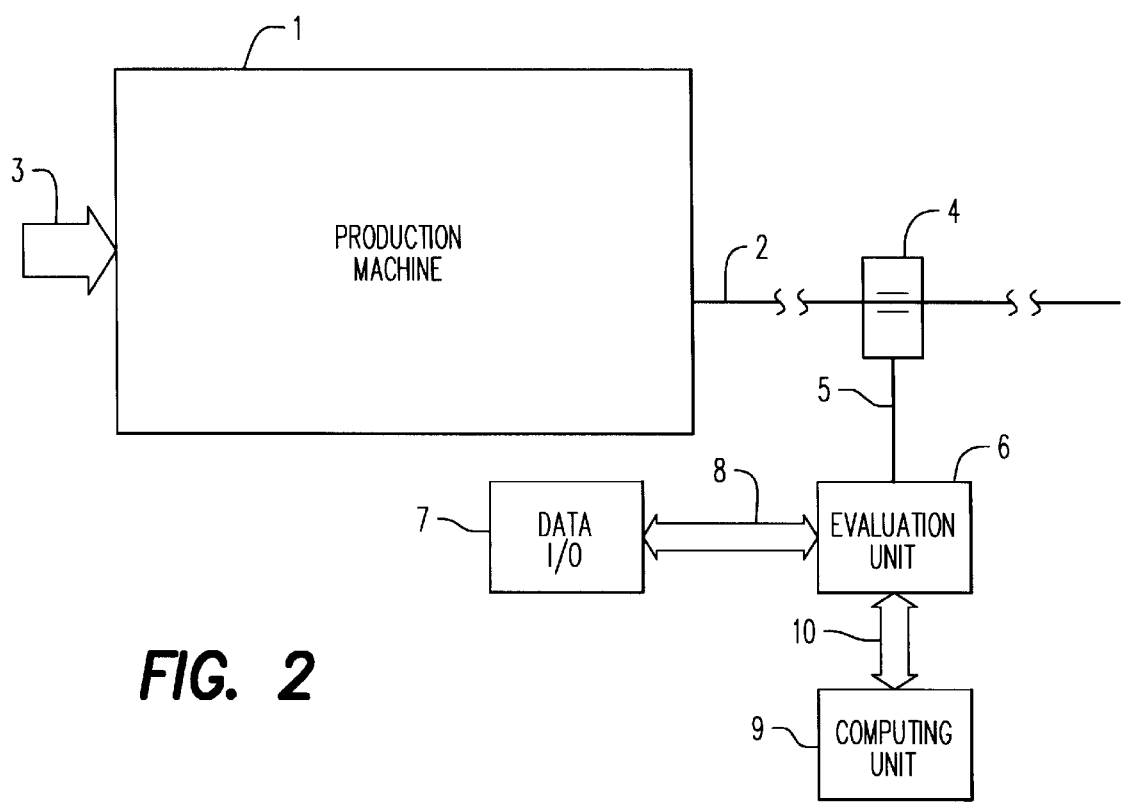
FIG. 2 shows a diagrammatic representation of an apparatus according to the invention in which samples of the products are recorded "off-line", FIGS. 3, 4, 5, 6 and 7 each show a different characteristic.

FIG. 2 shows an apparatus, such as already emerges in principle from FIG. 1, but with the difference that the sensor 4 is arranged outside the production machine 1 and not necessarily in the production line. Like elements therefore bear the same reference symbols as in FIG. 1. The arrangement according to FIG. 2 is consequently also suitable for carrying out a production process, in which the product is extracted from the process and investigated in a separate laboratory. This can preferably take place particularly as a result of the extraction of random samples.

Figure 3:
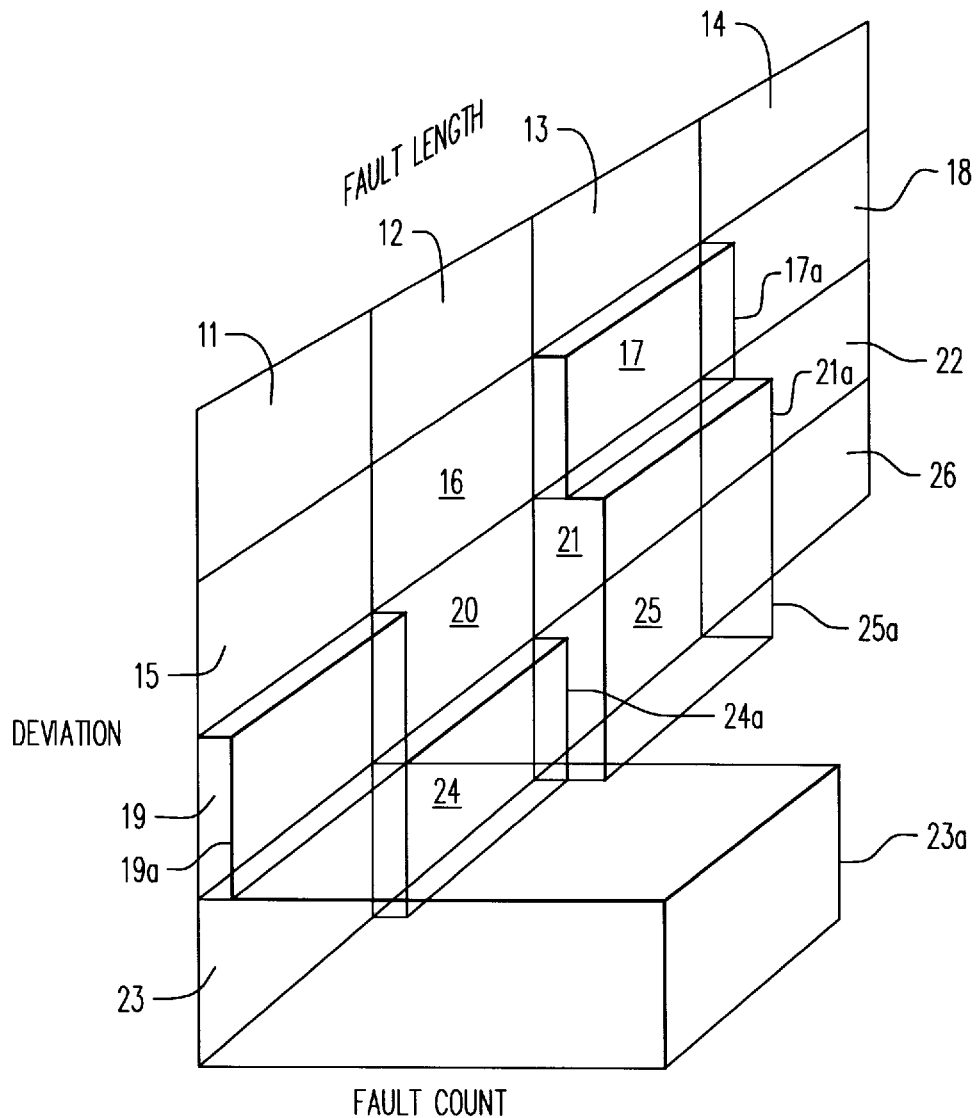
Figure 5:
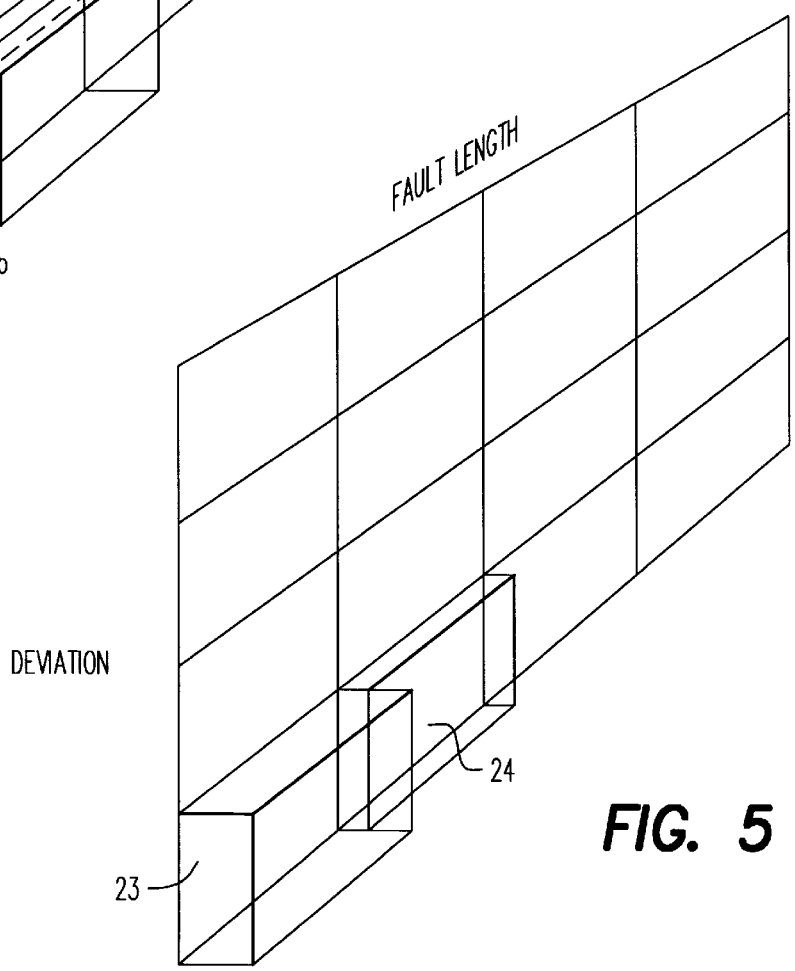

FIG. 3 shows a simplified representation of a known USTER CLASSIMAT table, such as is shown in more detail in the abovementioned Swiss Patent Specification No. 477, 573 (FIG. 5). A simplification here is that only sixteen fields bearing reference symbols 11 to 26 are shown. Each of these sixteen fields defines for a yarn a fault type which is characterized by a specific length and a specific deviation from the average cross-section. Each of the fields mentioned corresponds to a class of possible yarn faults and all the fields together give the classification field. Above the fields designated by 17, 19, 21, 23, 24 and 25 are plotted bars 17a, 19a, 21a, 23a, 24a and 25a, the height or length of which corresponds in each case to a number of measured faults in the respective class. The entirety of the bars 17a to 25a shown and the further bars of zero height not particularly emphasized here, such as, for example, above the fields 11 to 16, together give a characteristic or a fault pattern which is composed of count values for specific faults. A three-dimensional image representation is obtained in this form for the purpose of representing three parameters. For a yarn, these three parameters are the length of a fault, the cross-section or mass of a fault and the number of faults per class.

Figures 4A, 4B:
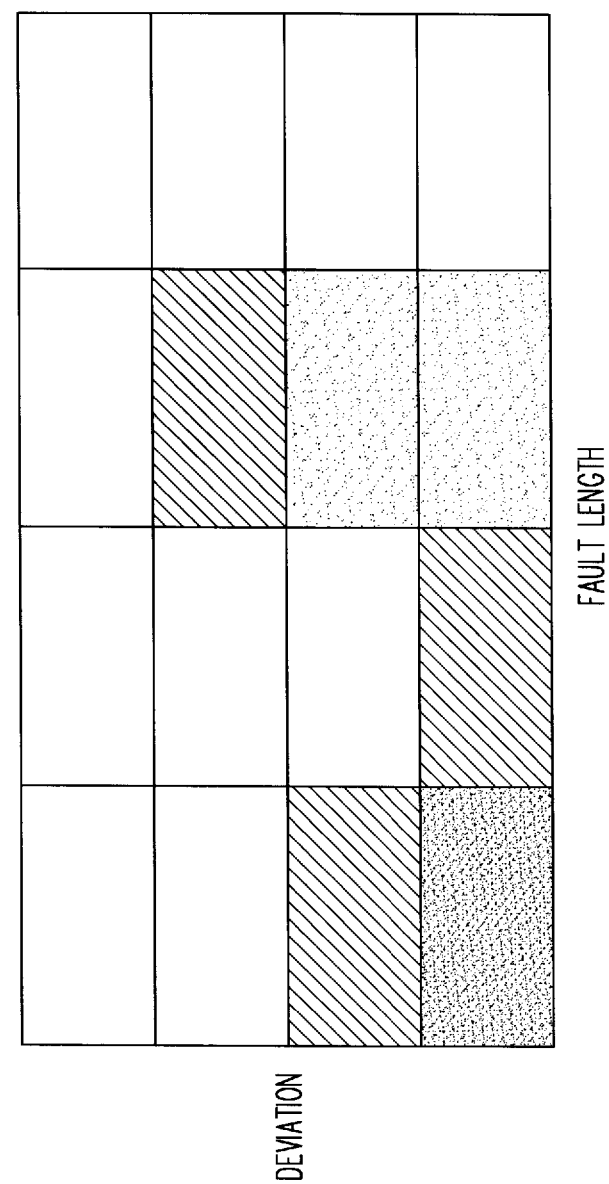

FIG. 4a shows a class division, such as is known from FIG. 3, but in which the count values are represented by patterns or colors instead of by bars. FIG. 4b shows an associated table which indicates which count values are to be assigned to which patterns or colors. This is for the same fault pattern which is shown in FIG. 3.

FIG. 5 shows a corresponding representation, such as is known from FIG. 3, but which indicates different faults or count values. Here, only count values for the fields 23 and 24 are indicated by two bars. These two count values give, for example, a characteristic of a fault-free yarn or, more precisely, of a yarn also having faults which can be recognized by means of the set limit values, but which are judged to be insignificant. This characteristic is to be considered as normal. Characteristics, such as are shown by the above-described FIGS. 3 and 4, deviate considerably from this and therefore point to faults which are unacceptable.

Figure 6:
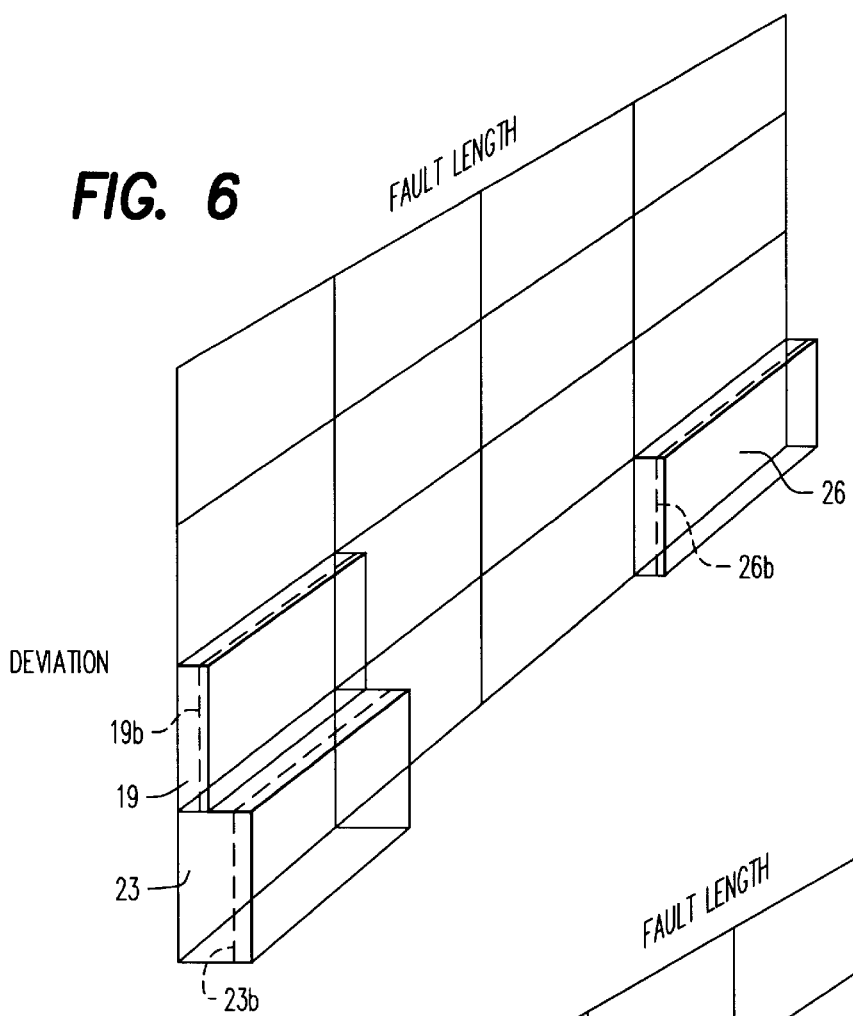

FIG. 6 shows count values for the fields or classes 19, 23 and 26 in the known representation. These again point to a different cause of the faults.

Figure 7:
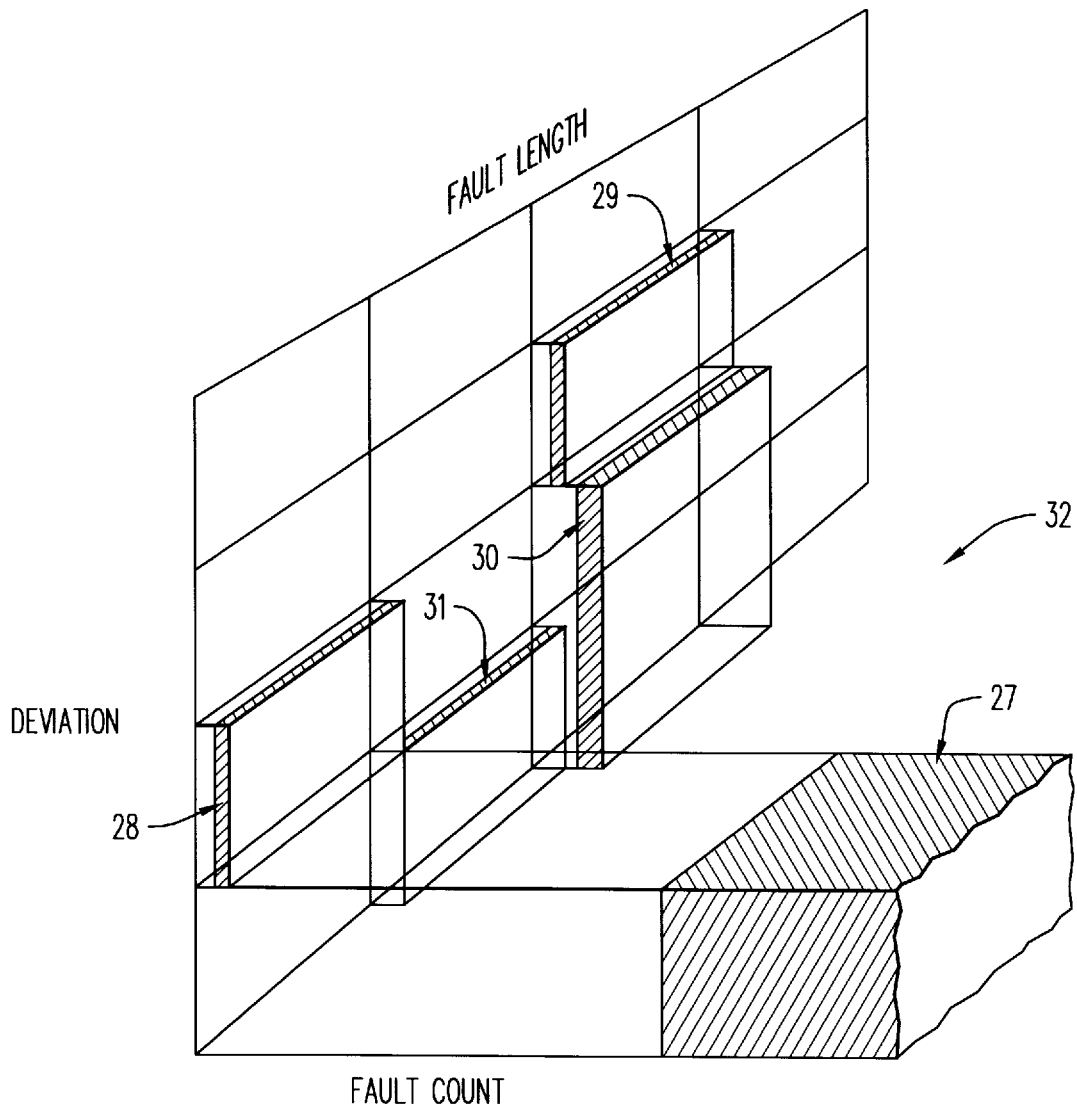

FIG. 7 shows a representation corresponding to that of FIG. 3, in which regions 27, 28, 29, 30 and 31 indicate a specific cause of faults. The count values of the individual classes must lie in these regions, so that a conclusion can be drawn as to the specific expected cause.

A comparison of FIGS. 3, 5 and 6 with one another shows three different characteristics or fault patterns with elevations and depressions. In FIG. 4, the three-dimensional fault pattern of FIG. 3 is converted into a two-dimensional fault pattern or image. Practical tests on the production apparatus 1 make it possible to determine which characteristic or which fault pattern of the abovementioned type is obtained as a result of specific variations on individual parts or subassemblies of the production apparatus. For example, practical tests on a rotor spinning machine showed that a fault pattern, such as that shown in FIGS. 3, 4 and 7, is obtained when the rotor is faulty. Contrary to this, FIG. 6 shows a fault pattern which is typically obtained when a draw-off roller is faulty. In contrast, FIG. 5 shows a fault pattern originating from a yarn which is deemed to be fault-free or which contains only those faults which do not point to any fault in the production process. The characteristic shown here, consisting of the count values assigned to the fields, constitutes a reference quantity for the characteristics which are shown in FIGS. 3, 6 and 7. Since a plurality of spinning stations are always working simultaneously in parallel with one another in a spinning machine, the other spinning stations can also supply the desired reference quantities or even average values can be formed from values of all the spinning stations, in order to derive the reference quantities for fault-free yarn from these. This emerges, for example, from FIG. 9.

Figure 9:
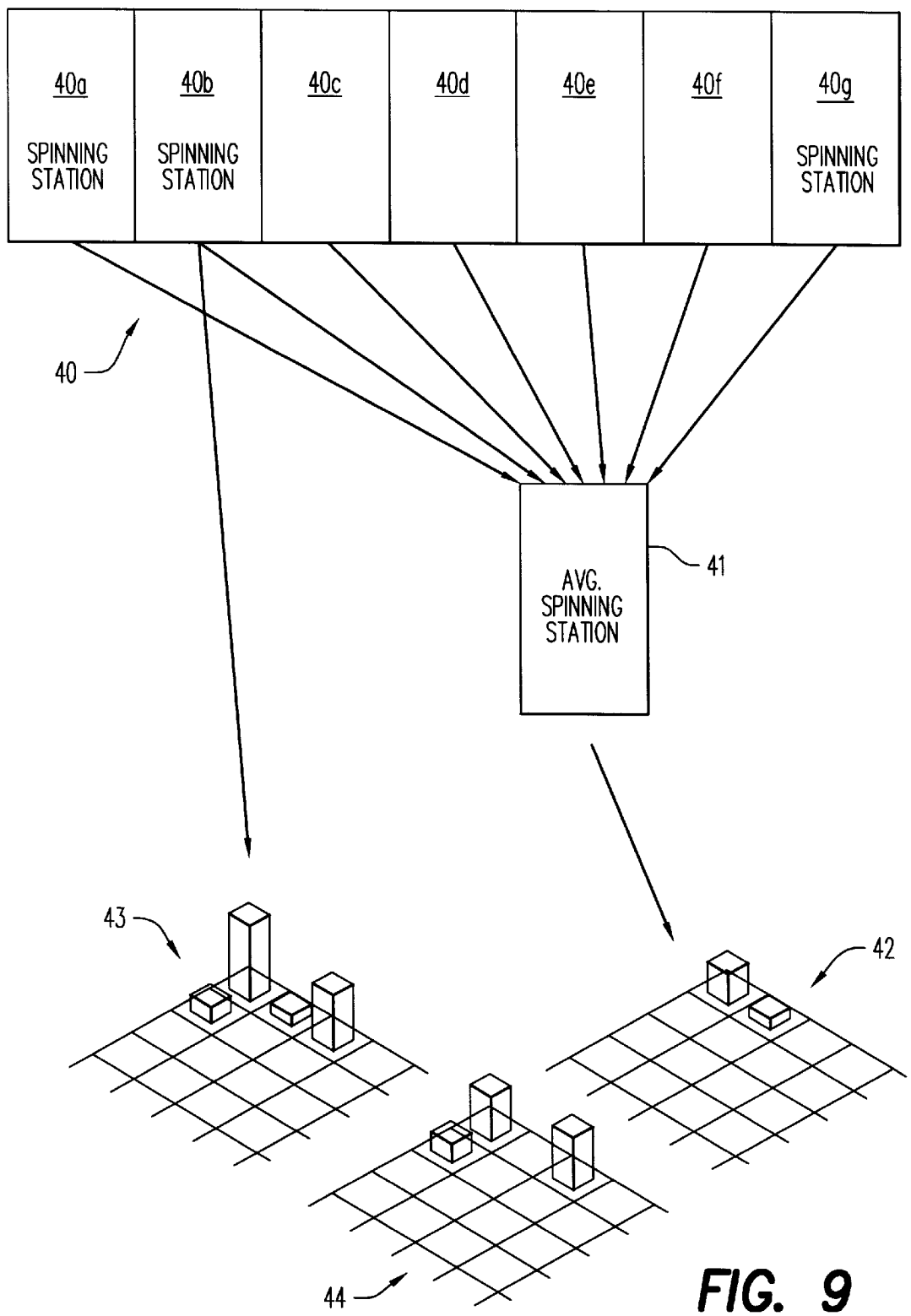
FIG. 9 shows a basic diagram of the invention.

FIG. 9 shows a diagrammatic representation of a production machine 40 which is designed, for example, as a spinning machine and which has a multiplicity of elements working in parallel and identical to one another, here the spinning stations 40a to 40g, which are fed with the same type of material. Each spinning station supplies in a way known per se a yarn having as identical properties as possible, such as could be supplied, for example, by an average spinning station 41 which is shown to represent the sum of the actual spinning stations 40a, etc. The average spinning station 41 supplies yarn which, in the fault test, yields a fault pattern, such as is designated by 42. The fault pattern 42 indicates permissible numbers of faults in the classes and corresponds approximately to that of FIG. 5. A spinning station 40b producing yarn with more faults, as intended to be represented by the fault pattern 43, has also contributed to this average fault pattern. The distinction or difference between the two fault patterns 43 and 42 yields a further fault pattern 44. For the identification of a fault cause in the spinning station 40b, it is possible to start directly from the fault pattern 43 or from the further fault pattern 44 and compare one of these fault patterns 43, 44 with a predetermined reference pattern. The reference pattern is closely analogous, ideally even identical to these fault patterns. It therefore indicates in the same fields a number of faults which is comparable to or which exceeds the fault patterns 43, 44.

Figure 10:
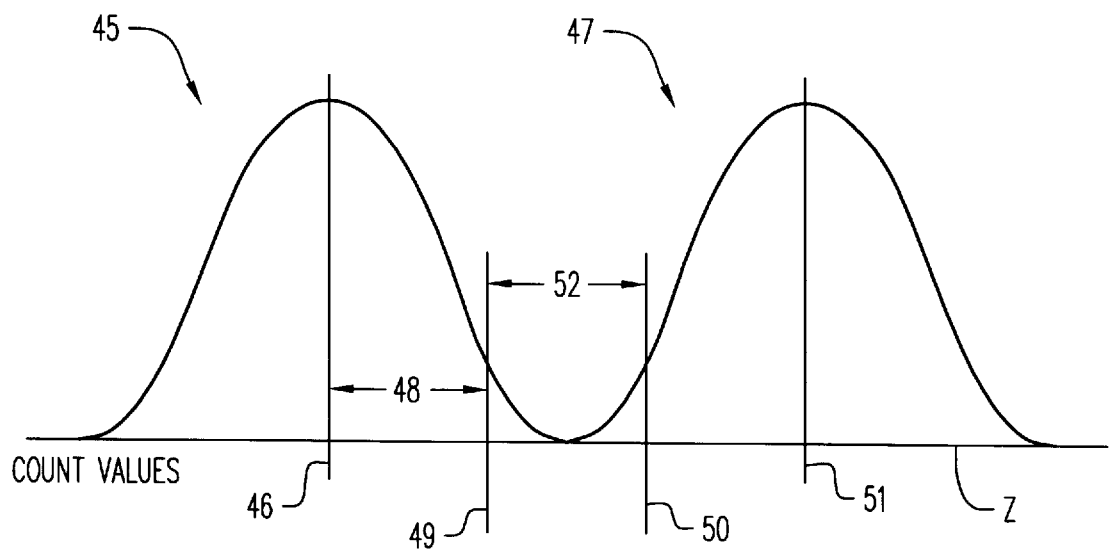
FIG. 10 shows frequency distributions of count values and of reference values.

FIG. 10 shows a representation of frequency distributions, such as can occur for count values of faults. An axis, on which count values are plotted, is designated by Z. Plotted vertically above this for such count values are the numbers which indicate how often such count values have been counted. A distribution 45 plotted around a count value 46 thus indicates that the count value 46 is the most frequent count value, but that, in addition, it was also possible to count further higher and lower count values. The distribution 45 belongs to the classification field of a reference pattern, whilst 47 denotes a distribution which belongs to the same classification field of the fault pattern. Indicated at a distance 48 from the count value in the direction of increasing values is a limit which is determined according to specific and selectable criteria and which is hereafter referred to as an upper confidence limit 49. In the same way, a lower control limit 50 relative to the count value 51 is indicated for the count values of the distribution 47 of the fault pattern. What is important, here, is that care is taken to ensure that the two control limits are at a positive distance 52 from one another. These control limits are important when the aim is to decide whether a relevant number of faults which is unusual is present in a class.

Figure 11:
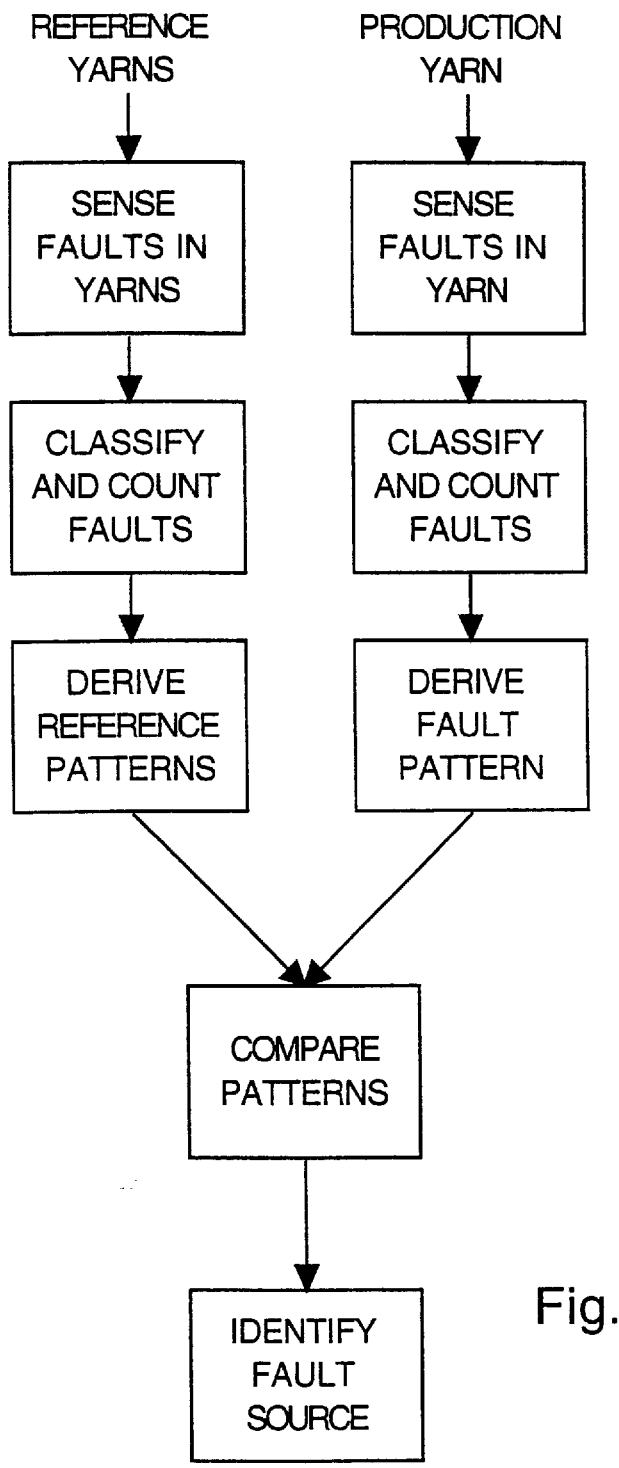
FIG. 11 is a flow chart of the operation of the invention.

For the method according to the invention, as shown in the flowchart of FIG. 11, it is first imagined that a production appliance is divided into parts 1a, 1b, 1c, etc., in which faults, signs of wear, soiling or other effects leading to losses of quality in the product 2 could be traced. Subsequently, a series of tests determines which characteristic fault images or fault patterns are obtained when one of the respective parts 1a, 1b, 1c, etc. has experienced undesirable variations. For this purpose, the faults in the product 2 are recorded via the sensor 4 and are compared, in the evaluation unit 6, with limit values or with value ranges which correspond to the classification. For each class of the classification, that is to say for each field 11 to 26 of FIG. 3, 4, 5, 6 or 7, those faults on the produced product which are deemed to be faults according to the classification are counted. These count values are statistically determined values. The laws of statistics apply to them, and consequently they can be dispersed and the dispersion can be represented in a distribution curve, for example the Poisson distribution curve or, in simplified form, the Gaussian distribution curve. If a large number of tests are carried out on the production machine and therefore a large number of values relating to a large quantity of produced material are obtained, then count values having a low dispersion occur and the distribution curve is correspondingly narrow. It is possible, from these count values which apply to a specific and, for example, artificially induced fault cause, to derive reference patterns or characteristics 32 (FIG. 7) which, from a combination of count values, apply to the fields of a classification field. Such reference patterns are represented in FIGS. 3, 4, 6, 7 and 8. The fault pattern 44 of FIG. 9 also belongs to these.

During the production of the product 2, for example a yarn, to some extent the same operations take place. The product 2 is monitored continuously by the sensor 4. If faults occur, these faults are assigned to predetermined classes and are counted in the individual classes. Thus, count values are determined continuously for each field 11 to 26. The count values assigned to the various classes together yield a fault pattern. The fault patterns are related to a specific yarn length, usually 100 km, by standardization or extrapolation. Subsequently, fault patterns containing typical and important indications are determined from the quantity of the existing fault patterns by an examination of similarity with the above-described reference patterns. Each reference pattern includes a specific indication as to a fault in the production process, and consequently a fault cause is determined.

However, there are also fault patterns which, although being determined as a result of the continuous monitoring of the product 2, nevertheless are permissible or do not point to faults in the production process. Such fault patterns are shown in FIG. 5 and in FIG. 9 (42). Such fault patterns always occur and it is necessary to take these into account in the evaluation. There are two possibilities for this.

A first possibility is to subtract count values of such fault patterns from the count values of the remaining fault patterns, as is described for FIG. 9. This procedure is justified when such insignificant faults have also already been subtracted from the significant faults during the preparation of the reference pattern. The fault patterns thus obtained then always relate to significant faults.

A second possibility is to assume that those fault patterns containing only insignificant faults are simply not to be considered any further, and to assume that these are always also present in all fault patterns. In that case, we obtain fault patterns with insignificant faults, for which there are no reference patterns, and fault patterns with significant faults, for which there are reference patterns. Only these latter fault patterns are then selected.

Since we are comparing here statistically determined values with further likewise statistically determined values, uncertainties which could lead to misinterpretations can occur. These are to be avoided by means of the method steps described below.

An upper control limit 49 is determined in relation to the count values 46 (FIG. 10) from each class which are determined from the series of tests. This control limit 49 is located above the actual count value 46 and is deemed to be the actual threshold value for this class. The reference profile, which is based on statistically determined values, is formed by these threshold values 49.

The lower control limit 50 is then determined in relation to the count values 51 determined from production or from individual production stations. This control limit 50 is located at a greater or lesser distance (measured in count values) below the actual count value. A method for this purpose is known, for example, from EP-A-0,365,901.

A significant value for the fault pattern is obtained for a class only when the count value from production is located with its lower control limit 50 above the upper control limit 49 of the corresponding value from the series of tests. Or, in other words, when a positive distance 52 occurs between the control limits, an alarm situation prevails in a class. So that conclusions can be drawn as to an actual fault cause, this must possibly apply to a plurality of classes which thus yield a fault pattern. The fault pattern must then be compared with the reference pattern, this being carried out by means of the abovementioned similarity examination.

Within the above-described method, the limit values, such as are represented in FIG. 6, for example by lines 19b, 23b and 26b, can be interpreted as lower control limits within the meaning of FIG. 10. Starting with these lower control limits, the count values can also be supplemented by a tolerance factor. Thus, regions 27 to 31, such as represented in FIG. 7, are obtained, and consequently also a characteristic fault pattern which can be indicated in the unit 7 or which can also be stored in the computer 9.

All the evaluations associated with the abovementioned method are carried out in the computing unit 9 which contains corresponding programs in the program memory and which extracts the measured values from the evaluation unit 6 or its data memory.

Figure 8:
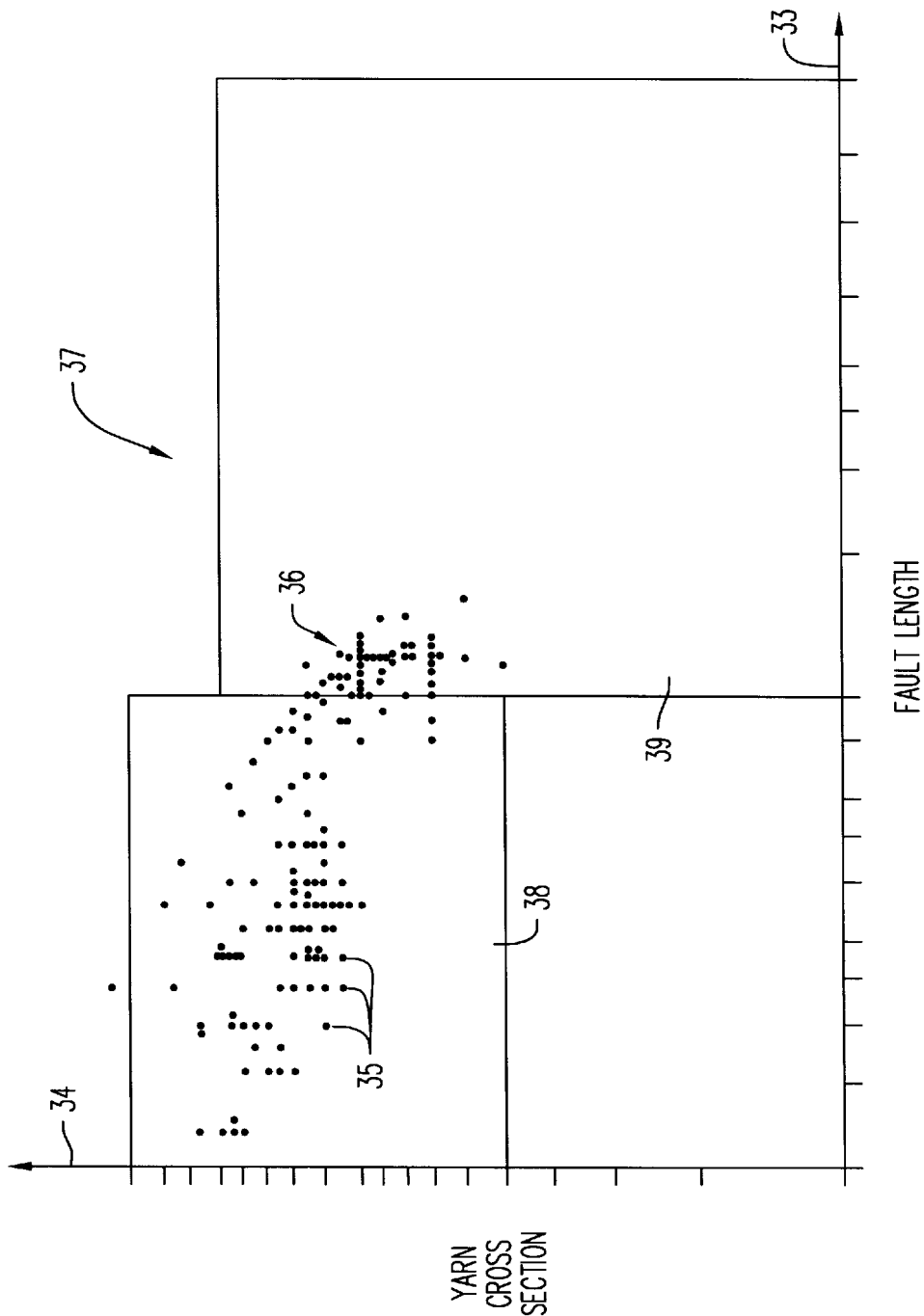
FIG. 8 shows a further diagrammatic representation of a characteristic.

FIG. 8 shows, as a further example, a classification with an infinitely fine resolution, that is to say the individual fields forming a class are infinitely small or, in other words, there is an infinite number of classes here. Values for the length of the faults may, for example, be plotted on an axis 33, whilst the increases in the cross-section of a yarn, which exactly make up the fault, are plotted on an axis 34. The individual dots 35 thus indicate a measured fault with its length and its cross-section. Since individual dots 35 do not reveal whether one or more faults having these parameters have been recognized, the faults are not counted. There is nevertheless thus obtained a fault image or a characteristic, the particular feature of which is that there occurs at a point 36 an accumulation of events, that is to say recognized faults, which in turn gives an indication as to a cause of a fault on a spinning machine. As shown here, it is also possible to subdivide the classification field 37 spanned by the two axes 33 and into regions 38 and 39, so that, for example, the relative position of accumulations 36 can be recognized more clearly. Such regions can also be used for a differentiated evaluation or weighting of the individual events. In order to obtain an indication as to a fault cause, in this instance too an examination of the fault pattern, such as is given by the accumulation 36, for similarity with a given reference pattern must be carried out.

Such a similarity examination between a fault pattern and a reference pattern can be conducted either with only binary values or also with discrete values. At all events, by means of the above-described method steps, the problem of a textile nature has been reduced to a problem of so-called symbol recognition. Accordingly, each fault pattern and each reference pattern can be interpreted as a symbol. The fault pattern is then compared, that is to say checked for identity, with the reference pattern by symbol-recognition means known per se. There are many known methods for this purpose.

For fault and reference patterns present in binary form, such as, for example, that of FIG. 8, for example a method, such as described by R. Lippman in "An Introduction to Computing with Neural Nets" from IEEE, Acoustics, Speech and Signal Processing Magazine, April 1987, pages 4–22, is suitable. Such methods are known and implemented, for example, for appliances which carry out character recognition.

Many methods for pattern recognition can be used for fault and reference patterns which are present in the form of discrete count values. One of these is described in the book by T. Tilli: "Mustererkennung mit Fuzzy Logic" ["Pattern Recognition with Fuzzy Logic"], Franzis Verlag, 1993. Of course, it is also possible to develop specific algorithms which perform the set function and which specify the exact rules relating to the permissible and impermissible deviations between fault patterns and reference patterns.

It is to be noted, furthermore, that not only thick places constitute faults in a yarn. Thin places are also to be considered as faults which allow a statement to be made on fault sources on the spinning machine. In addition to the classification fields shown for two or three parameters, classification fields representing more than three parameters are also conceivable. Such a further parameter, which is also important in this respect, is the length of the fault-free yarn between individual faults or the distance between the individual faults. At the same time, with regard to freedom from faults, a distinction can also be made between distances between faults of the same type and distances between faults of different types. The larger the number of such parameters, the more differentiating is the indication of the cause of faults. However, the outlay in terms of analysis also increases as a consequence. It is also possible to work with only one parameter. In the representation according to FIG. 3, this would mean, for example, that the field is subdivided only into columns or rows, and that the count values of the bars 17a, 21a and 25a are distributed over the entire column when a division according to columns is made.

The method according to the invention can also be carried out in a subsequent production stage, in order to locate faults in the preceding production stage. For example, for yarns, this can be carried out in the winding room, in order to find causes of faults in the preceding ring-spinning stages.

In practice, faults caused by the raw material that is used and faults caused by the production process can occur together. These can be kept apart from one another by means of the present invention, for the machine faults always generate characteristic fault patterns. Although these can be distorted by the raw-material faults, the machine faults nevertheless always yield recognizable fault patterns. In the case of production processes running in parallel, therefore, it can be advantageous to separate out fault patterns pointing to impermissible faults in a first selection step by comparing these with an average fault pattern which indicates permissible faults in a manner averaged over all the production processes. Only fault patterns deviating from this are then compared with predetermined reference patterns.

What is claimed is:

1. A method for determining production-related causes of faults in textile materials, comprising the steps of:

recording at least one parameter associated with faults in textile materials whose causes are known;

classifying the faults whose causes are known according to the recorded parameter;

deriving respective reference patterns of the classified faults for the known causes;

detecting faults in textile materials whose cause is unknown and classifying the detected faults whose causes are unknown according to said parameter to obtain a fault pattern;

comparing said fault pattern to said reference patterns; and identifying a cause of a detected fault whose cause was unknown from the comparison of the reference patterns and the fault pattern.

2. The method of claim 1 wherein a pattern is determined from the quantity of detected faults in said classifications.

3. The method of claim 2 further including the step of establishing a preset value for the number of detected faults with respect to a quantity of yarn.

4. The method of claim 1 wherein said faults are detected in textile materials from a plurality of textile production machines that operate in parallel with one another, further including the steps of determining a fault pattern for each of said machines, comparing said fault patterns with a reference pattern, and determining a cause of a fault from said comparison.

5. The method of claim 1 wherein the step of identifying the cause of a fault is carried out by means of a pattern recognition procedure.

6. Apparatus for determining production-related causes of faults in textile materials, comprising:

means storing reference fault patterns which respectively relate to causes of faults in textile materials;

means for recording individual faults in a textile material;

means for classifying the recorded faults;

means for deriving a fault pattern from the classified faults; and means for comparing a derived fault pattern with the stored reference patterns to identify the cause of a detected fault.

7. Apparatus for determining production-related causes of faults in textile materials, comprising:

means storing reference fault patterns which respectively relate to causes of faults in textile materials;

means for recording individual faults in a textile material, including means for counting the faults, means for classifying the recorded faults;

means for deriving a fault pattern from the classified faults; and means for comparing a derived fault pattern with the stored reference patterns to identify the cause of a detected fault.

8. The apparatus of claim 6 wherein said comparing means comprises a pattern recognition device.

9. A method for determining production-related causes of faults in textile materials, comprising the steps of:

recording at least one parameter associated with faults in textile materials whose causes are known;

classifying the faults whose causes are known according to the recorded parameter;

deriving respective reference patterns of the classified faults for the known causes;

detecting faults in textile materials whose causes are unknown from a plurality of textile production machines that operate in parallel with one another, and classifying the detected faults whose causes are unknown according to said parameter to obtain a fault pattern for each of said machines;

comparing said fault patterns to said reference patterns;

identifying a cause of a detected fault whose cause was unknown from the comparison of the reference patterns and the fault patterns;

deriving an average fault pattern from the fault patterns for each of said machines;

comparing the fault patterns for each of said machines with said average fault pattern;

identifying a significant deviation in a fault pattern for a machine from said average fault pattern; and determining the cause of a fault whose cause was unknown from a fault pattern containing a significant deviation.

* * * * *